United States Patent [19]

Capelli

[11] Patent Number: 4,933,178

[45] Date of Patent: Jun. 12, 1990

[54] METAL-BASED ANTIMICROBIAL COATING

[75] Inventor: Christopher C. Capelli, Kenosha, Wis.

[73] Assignee: Biointerface Technologies, Inc., Madison, Wis.

[21] Appl. No.: 254,710

[22] Filed: Oct. 7, 1988

[51] Int. Cl.$^5$ .................... A61K 31/74; A01N 43/36; C07C 5/00; C08J 6/00

[52] U.S. Cl. .................................. 424/78; 424/405; 424/422; 424/423; 424/424; 424/617; 424/618; 523/122; 523/112; 523/113; 604/266; 604/265

[58] Field of Search ................ 523/122, 112, 113; 424/618, 617, 422, 423, 424, 78, 405; 604/266, 265

[56] References Cited

U.S. PATENT DOCUMENTS

| | | | |
|---|---|---|---|
| 4,054,139 | 10/1977 | Crossley | 604/265 |
| 4,344,431 | 8/1982 | Yolles | 128/260 |
| 4,392,848 | 7/1983 | Lucas et al. | 604/265 |
| 4,479,795 | 10/1984 | Mustacich et al. | 604/265 |
| 4,581,028 | 4/1986 | Fox, Jr. et al. | 604/265 |
| 4,592,920 | 10/1986 | Murtfeldt | 604/265 |
| 4,677,143 | 6/1987 | Laurin et al. | 523/122 |

*Primary Examiner*—Joseph L. Schofer
*Assistant Examiner*—Carmen Pili-Curtis
*Attorney, Agent, or Firm*—Foley & Lardner, Schwartz, Jeffery, Schwaab, Mack, Blumenthal & Evans

[57] ABSTRACT

A medical device with an antimicrobial coating that is safe, effective, photostable and readily manufacturable can be produced by applying a composition to at least one body fluid-contacting surface of the device such that a solid coating is provided on that surface, the coating composition comprising an oligodynamic metal salt of a sulfonylurea, a polymeric material, at least one acid compound selected from the group consisting of a water-soluble carboxylic acid and water-insoluble carboxylic acid, and a carrier liquid in which foregoing components are soluble. The antimicrobial coating accommodates variation in the release of antimicrobial metal ions as a function of the intended use for a medical device to which the coating is applied.

9 Claims, No Drawings

METAL-BASED ANTIMICROBIAL COATING

BACKGROUND OF THE INVENTION

The present invention relates generally to antimicrobial agents and, in particular, to metalbased antimicrobial agents suitable for coating medical devices.

Many medical procedures involve the placement of devices, such as catheters, endotracheal tubes, protheses, grafts, sutures, dressings and implants, in the human body. Infection is a common complication associated with the use of such devices. Various techniques for alleviating infection in this regard are commonly employed, including topical and systemic applications of antibiotics. Nonetheless, such techniques have not been particularly effective in preventing infection associated with devices intended to remain within the body, or in contact with bodily fluids, for an extended period of time.

Antimicrobial agents are chemical compositions that inhibit microbial growth or kill bacteria, fungi and other microorganisms. Different inorganic and organic substances display antimicrobial activity. Among the simple organic substances that possess antimicrobial activity are carboxylic acids, alcohols and aldehydes, most of which appear to act by protein precipitation or by disruption of microbial cell membrane.

The antimicrobial activity of inorganic substances is generally related to the ions, toxic to other microorganisms, into which they dissociate. The antimicrobial activity of various metal ions, for example, is often attributed to their affinity for protein material and the insolubility of the metal proteinate formed. Metal-containing salts are thus among the inorganic substances that act as antimicrobial agents.

Metal inorganic salts, including simple salts of metal cations and inorganic anions like silver nitrate, are often soluble and dissociable and, hence, offer ready availability of potentially toxic ions. But such salts may be quickly rendered ineffective as antimicrobial agents by the combining of the metal ion with extraneous organic matter or with anions from tissue or bodily fluid. As a consequence, prolonged or controlled bacteriostatic and bacteriocidal activity is lost.

Metal salts or complexes of organic moieties such as organic acids, on the other hand, are often less soluble and, therefore, are less dissociable than the soluble metal inorganic salts. Metal organic salts or complexes generally have a greater stability with respect to extraneous organic matter, and anions present in the environment of the living cell than metal inorganic salts, but have less toxic potential by virtue of their greater stability. The use of heavy metal ions with polyfunctional organic ligands as antimicrobial agents has been disclosed, for example, in U.S. Pat. No. 4,055,655.

The silver (I) ion is an example of a metal ion known to possess antimicrobial activity. The use of silver salts, including both inorganic and organic ligands, as antimicrobial agents has long been known in the prior art. The dissociation of the silver salt provides silver ions which provide the antimicrobial activity. Silver ions react with a variety of anions as well as with chemical moieties of proteins. Precipitation of proteins, causing disruption of the microbial cell membrane and complexation with DNA, is likely the basis of the antimicrobial activity. Silver ions in high concentration will form insoluble silver chloride and thereby deplete chloride ions in vivo.

Silver sulfadiazine is an organo-silver salt which is currently widely used as a topical antimicrobial agent, as discussed by Fox, "Silver Sulfadiazine - A New Topical Therapy for *Pseudomonas* in Burns," *Archs. Surg.* 96: 184–88 (1968). The antimicrobial activity of silver complexes with fatty acids has also been disclosed, for example, in U.S. patents No. 3,255,222 and No. 3,385,654.

But silver salts, like a number of other metal salts, are also light sensitive, in that exposing them to light causes a discoloration or black staining associated with the deposition of reduced silver. Silver salts are usually most sensitive to blue light or higher energy electromagnetic radiation such as ultraviolet rays.

Both the antimicrobial activity and the light stability of a silver salt are dependent upon its stability and solubility. In general, a large dissociation constant generally leads to discoloration, while a small dissociation value leads to minimal growth inhibition or toxic potential due to the low concentration of available silver ions.

High solubility also promotes discoloration or black staining. Low solubility, on the other hand, results in a low availability of silver ions. Thus, it appears likely that a silver salt with a low solubility and a medium-range dissociation constant will be light stable.

In general, prior attempts at the use of antimicrobial metallic compositions, including silver salts, appear to have encountered problems of two types. On the one hand, there are metal compounds that have a high degree of dissociation such that toxic metal ions are rapidly and copiously made available, due to rapid dissociation and consequent formation of ionized species. These species saturate all available ligands and are thereby inactivated in a very narrow time frame. This obviates residual killing power, rendering such compositions relatively ineffective as antimicrobial agents over prolonged periods of time. On the other hand, metal compounds which are relatively stable provide only minimal amounts of ionized species over the normal physiological pH range. They provide, therefore, minimal growth inhibition or toxic potential, due to their low degree of dissociation.

The use of metal-based antimicrobial compositions applied as coatings on medical devices poses further problems. The matrix in which the antimicrobial agent is held to form the coating must be permeable to allow diffusion of the antimicrobial metal ions out of the matrix in to the environment. The solubility of the antimicrobial agent in a suitable solvent must be sufficient so that the resulting coating has a concentration of agent which will yield antimicrobial activity.

If the solubility is very low, a coating with a large surface area may be required to obtain an active amount of antimicrobial agent. A thicker antimicrobial coating, for example, of greater than 1 mm in thickness, may be required to obtain an active amount of antimicrobial agent. The dissociation of the metallic and the diffusion rate of the metal ions out of the matrix, i.e., the release of ions, must correspond to the medical use of the device. For devices that will be in contact with the body for extended times, a slow, steady release of metal ions would be appropriate. For devices with a short lifetime, quicker release may be most appropriate.

If a silver-based compound is to be used, it must not undergo chemical reaction upon exposure to light or, at least, the rate of such a photoreaction must be slow compared to the duration of contact between the medical device and body tissue or fluid. Also, the available silver ion concentration should not be so high as to deplete chloride from the environment.

The use of silver sulfadiazine in this context is of particular interest since both the silver ion and the sulfadiazine one of the sulfonamides or "sulfa" drugs, have antimicrobial properties. Silver sulfadiazine is a polymer wherein each silver ion is tetracoordinated and surrounded by three different deprotonated sulfa molecules; each sulfa molecule, in turn, binds three different silver ions. See Bult, "Silver Sulfadiazine and Related Antibacterial Metal Sulfanilamides; Facts and Fancy," Pharmacy Intl. December, 1982, at pages 400–04.

Silver sulfadiazine is formed by combining equal molar amounts of silver nitrate and sodium sulfadiazine solutions. Its dissociation constant (pK) is 3.57 at a pH of 7.4, an ionic strength of 0.1 and a temperature of 25° C. The compound is almost insoluble in water and in organic solvents, a feature attributable to its polymeric character. It does not darken upon exposure to light and does not deplete chloride from tissue fluid. It is likely that its insolubility and medium-range stability constant are responsible for photostability and lack of chloride depletion.

But low solubility can result in minimal toxic potential to microbes. The very low solubility of silver sulfadiazine also limits its incorporation into synthetic or natural polymeric materials. Multiple layers of coatings are generally required to achieve a sufficient amount of the silver sulfadiazine for antimicrobial activity.

Despite many prior attempts at imparting antimicrobial properties to medical devices, a coating composition has yet to be demonstrated that provides for variation in the release of antimicrobial agent, according to the particular use of the medical device, and for sufficient solubility to allow the use of thin coatings.

SUMMARY OF THE INVENTION

It is therefore an object of the present invention to provide a medical device with an antimicrobial coating that is safe, effective, photostable and readily manufacturable.

It is also an object of the present invention to provide an antimicrobial coating that can impart antimicrobial properties to a medical device with a single coating, dipping or spraying.

It is a further object of the present invention to provide an antimicrobial agent that accommodates variation in the release of antimicrobial metal ions as a function of the intended use for a medical device to which the antimicrobial agent is applied.

It is yet another object of the present invention to provide a method for rendering a medical device infection-resistant, which method avoids the need for multiple applications, from separate solutions, of material to the device.

In accomplishing the foregoing objects, there has been provided, in accordance with one aspect of the present invention, a medical device that comprises (a) a substrate presenting a surface suitable for contact with a body fluid and (b) an antimicrobial coating provided on the body fluid-contacting surface, wherein the coating comprises an oligodynamic metal salt of a sulfonylurea, a polymeric material and at least one acid compound selected from the group consisting of a water-soluble carboxylic acid and a water-insoluble carboxylic acid. In a preferred embodiment, the sulfonylurea is tolbutamide, acetohexamide, tolazamide or chlorpropamide.

In accordance with another embodiment of the present invention, an antimicrobial coating composition has been provided that comprises an oligodynamic metal salt of a sulfonylurea, a polymeric material and at least one acid compound from the group consisting of a water-soluble carboxylic acid and a water-insoluble carboxylic acid. In a preferred embodiment, the acid compound is present in an amount sufficient to render a coating comprised of the composition light-stable and to effect controlled release of silver ions from that coating.

There has also been provided, in accordance with yet another embodiment of the present invention, a method for preparing a microbial-resistant medical device which presents a surface suitable for contact with a body fluid. The method comprises the steps of (a) preparing an antimicrobial composition comprising (i) an oligodynamic metal salt of a sulfonylurea, (ii) a polymeric material, (iii) at least one acid compound selected from the group consisting of a water-soluble carboxylic acid and a water-insoluble carboxylic acid, and (iv) a carrier liquid in which components (i), (ii) and (iii) are soluble; and (b) applying the composition to at least the body fluid-contacting surface of the device such that a solid coating is provided on the latter surface. Step (b) of the method can be accomplished, in a single application step, by painting or spraying the antimicrobial composition onto the medical device, or by dipping the device (or a portion of the device) into the composition.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Pursuant to the present invention, an antimicrobial coating composition is provided which incorporates an oligodynamic sulfonylurea/metal salt and which can be used to impart antimicrobial properties to medical devices, including catheters and other types of implanted devices. An acid compound is added to improve light stability and to modulate the release of metal ions which impart antimicrobial activity. A metal-containing antimicrobial coating composition within the present invention is light stable, even when the metal involved is silver, and has a release rate of metal ions that can be varied, as required by the particular medical use.

In the context of the present description, the term "oligodynamic" is used to denote an agent, particularly a salt or a metal ion it yields upon dissociation, that is active in very small quantities. As indicated above, the oligodynamic nature of silver and silver salts is well known, and other metals, including gold, zinc, platinum and copper, and their salts are similarly characterized. A review of oligodynamic metals is given in DISINFECTION, STERILIZATION AND PRESERVATION, Chapters 24 and 28 (Lea & Fibiger, Philadelphia 1968), the contents of which are hereby incorporated by reference.

The antimicrobial coating composition according to the present invention comprises a metal-containing sulfonylurea compound, along with one or both of a water-soluble and a water-insoluble carboxylic acid compound, in a polymeric matrix. A single coating of the composition can provide antimicrobial activity.

Sulfonylurea compounds that are suitable for use in accordance with the present invention include acetohexamide, tolazamide and chloropropamide. The general structural formula for sulfonylureas is:

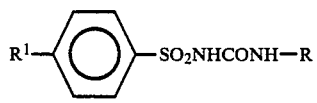

where R is typically an alkyl or cycloalkyl group and $R^1$ is a methyl, an ethoxy or a halogen group. A representative metal-containing sulfonylurea compound suitable for use in the present invention is silver tolbutamide (AgTol), a white compound formed when equal molar amounts of silver nitrate and sodium tolbutamide, both in aqueous solution, are mixed. AgTol incorporates a tolbutamide ligand that is a sulfonylurea, tolbutamide having a molecular structure represented by the formula:

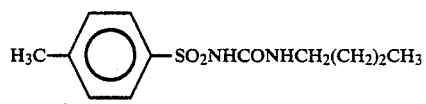

The sulfonylureas are known for their hypoglycemic properties, but none are reported to be antimicrobial. Accordingly, tolbutamide is understood not to contribute any antimicrobial activity to silver tolbutamide, in contrast to the sulfadiazine component of silver sulfadiazine.

AgTol has a medium value dissociation constant estimated to be greater then pK =3.3. It does not deplete chloride from tissue fluid, but is soluble in a variety of organic solvents, including solvents containing polymers. The solubility of AgTol, which is not a polymer, is considerably greater than that of silver sulfadiazine. AgTol is not photostable when present in a coating, yet is observed to be light stable as a solid. The light instability of AgTol appears to be related both to the lack of stabilization of the silver ion in the compound and the nonpolymeric nature of AgTol.

It has been discovered that the light sensitivity of metal-containing sulfonylurea compounds like AgTol can be improved by the addition of carboxylic acids to a metal sulfonylurea salt/polymer matrix. Although the precise mechanism for this effect is unclear, it is believed that a carboxylic acid acts as a second ligand for the metal ion. Typically, the greater the number of ligands, the greater the stability of the complex. It is believed that the increased stability changes both the solubility and the dissociation constant of the metal salt and renders it more photostable.

One unexpected aspect of the present invention is the capability provided to vary the rate of release of metal ions from a metal sulfonylureacarboxylic acid complex by varying the nature and the amount of the carboxylic acid used. A hydrophobic (water-insoluble) carboxylic acid, such as a fatty acid, improves light stability but lowers antimicrobial activity, by decreasing the release rate of silver ions from the coating. On the other hand, a hydrophilic (water-soluble) carboxylic acid like citric acid enhances light stability of the complex without lowering antimicrobial activity, i.e., the acid compound does not affect the rate at which silver or some other oligodynamic metal is released from the sulfonylurea compound.

By changing the ratios of these two types of carboxylic acids, pursuant to the present invention, one can achieve a broad range of antimicrobial activities while maintaining light stability. This is important because antimicrobial activity must be adjusted in order for many medical devices to accommodate differing periods of time when the devices will be implanted or otherwise in contact with body tissue.

Thus, an antimicrobial coating according to the present invention includes a metal-containing sulfonylurea, preferably AgTol, and at least one of a water-soluble carboxylic acid and a water-insoluble carboxylic acid in a polymer matrix. The polymer material forming the matrix should permit suitable diffusion of the metal ions out of the matrix. An acceptable permeability is reflected, for example, in a high moisture-vapor transmission (MVTR) value, preferably in the range of about 100 to 2500 g/m²/24 hours/mil of membrane thickness. Polymers that can be used in this context include polyurethane, polyvinylchloride, nylon, polystyrene, polyethylene, polyvinyl alcohol, polyvinyl acetatae, silicone and polyester.

Exemplary of solvents which can be employed in the present invention are those characterized by a solubility parameter, expressed in terms of $(Cal/cn^2)^{\frac{1}{2}}$, of between about 9 and 12, such as (Cal/cm2) tetrahydrofuran, benzene, diacetone alcohol, methyl ethyl ketone, acetone and N-methyl pyrrolidone.

A variety of water-insoluble carboxylic acids are conveniently employed in the present invention, including fatty acids, such as stearic acid, capric acid, lauric acid, myrisic acid, palmitic acid and arachidic acid, as well as cholic acid, deoxycholic acid, taurocholic acid and glycocholic acid. By the same token, numerous water-soluble carboxylic acids are suitable, such as citric acid, gluconic acid, glutamic acid, glucoheptonic acid, acetic acid, propionic acid and butyric acid.

The molar amount of each type of carboxylic acid can be varied, preferably from about 0 to about 2 mole per mole of metal-containing sulfonylurea. The respective amounts used of water-soluble and water-insoluble acids will depend upon the level of antimicrobial activity desired from the coating.

The coating can be applied to a medical device by dipping in the antimicrobial solution and thereafter allowing the solvent to evaporated. Both inside and outside surfaces can be coated. Alternatively, the medical articles can be sprayed with the mixture and the solvent allowed to evaporated. Likewise, the medical device can be painted with the solution, and the solvent allowed to evaporate. All coating processes can be carried out at room temperature, but evaporation of solvent can be hastened by oven drying, for example, at about 40° C. for some 90 minutes. The thickness of the coating, regardless of coating method used, is preferably about 0.1 mil.

Alternatively, the rate of release of metal ions can be adjusted by using multiple coating layers characterized by differing carboxylic-acid components. A first layer, applied as described above, can thus incorporate a water-insoluble carboxylic acid and a second, overlying layer a water-soluble carboxylic acid. In such an arrangement, there is an initial high rate of release of metal ions from the latter layer, as the water-soluble carboxylic acid does not affect the antimicrobial activity of the metal-containing sulfonylurea. The release from the underlying layer, on the other hand, is slower, due to the presence of the water-insoluble carboxylic acid, which effects long-term release.

The present invention will be further described by reference to the following, illustrative examples. As elsewhere in this description, process steps described below were carried out at room temperature and atmospheric pressure, unless otherwise specified.

Example 1. Determination of Photostability and Microbial Toxicity.

Compositions within the present invention were tested in a variety of ways in order to determine light sensitivity and antimicrobial action.

To ascertain photostability, catheters coated with antimicrobial compositions according to the present invention were prepared using either citric acid, a water-soluble carboxylic acid, or stearic acid, a water-insoluble carboxylic acid, and exposed to indirect sunlight for up to 48 hours, thereby to determine if discoloration occurred. The results of this experiment are summarized in the table below.

TABLE 1

Effect of Carboxylic Acids on Light Sensitivity

| Compound | Molar Ratio | 1 Hr | 24 Hrs | 48 Hrs |
|---|---|---|---|---|
| Ag:Tol | 1:1 | clear | brown | dark brown |
| Ag:Tol:stearic acid | 1:1:1 | clear | clear | s.d.* |
| Ag:Tol:citric acid | 1:1:1 | clear | clear | s.d.* |

*slight discoloration

Only a slight discoloration of the coating was observed, even after 48 hours of exposure, when either stearic acid or citric acid was added to silver tolbutamide. The addition of a carboxylic acid to silver tolbutamide, pursuant to the present invention, thus improved light stability significantly.

The availability of metal ions for antimicrobial action was also ascertained, with respect to the addition of carboxylic acids to the silver tolbutamide, by a conventional zone-of-inhibition test, using either *Escherichia coli* or *Staphylococcus epidermidis*. The results, as summarized in Table 2, demonstrated that the addition of a water-insoluble acid (stearic acid) modulates the availability of metal ions for antimicrobial purposes. When the molar ratio of stearic acid was twice that of silver tolbutamide, the zone of inhibition was reduced to virtually zero. On the other hand, the addition to the silver tolbutamide of a water-soluble acid (citric acid) did not affect the size of the zone of inhibition.

TABLE 2

Effects of Carboxylic Acids on Antimicrobial Activity

| Compound | Molar Ratio | Zone of Inhibition (mm) S. epidermidis | E. coli |
|---|---|---|---|
| AgTol | 1:0 | 10 | 7 |
| AgTol:stearic acid | 1:0.3 | 10 | 6 |
| AgTol:stearic acid | 1:0.5 | 8 | 7 |
| AgTol:stearic acid | 1:1 | 5 | 4 |
| AgTol:stearic acid | 1:2 | 0 | 0 |
| AgTol:stearic acid:citric acid | 1:2:0 | 0 | 0 |
| AgTol:stearic acid:citric acid | 1:2:0.5 | 5 | 4 |
| AgTol:stearic acid:citric acid | 1:2:1 | 7 | 5 |
| AgTol:stearic acid:citric acid | 1:2:2 | 10 | 5 |
| AgTol:stearic acid:citric acid | 1:1:0 | 5 | 4 |
| AgTol:stearic acid:citric acid | 1:1:1 | 11 | 5 |

TABLE 2-continued

Effects of Carboxylic Acids on Antimicrobial Activity

| Compound | Molar Ratio | Zone of Inhibition (mm) S. epidermidis | E. coli |
|---|---|---|---|
| AgTol:stearic acid:citric acid | 1:1:2 | 12 | 5 |

Example 2. Production of a Medical Device within the Present Invention.

To prepare a medical device with the antimicrobial coating composition according to the present invention, aqueous solutions of silver nitrate and sodium tolbutamide were mixed in equimolar amounts to precipitate about 100 g of silver tolbutamide from approximately one liter of solution. The silver tolbutamide precipitate was removed from the solution and dried in a conventional manner.

The dried silver-tolbutamide precipitate was then dissolved in sufficient 1-methyl-2-pyrrolidine (M-Pyrol, a product of GAF Corp.) to form a 20% solution (weight/volume). This silver tolbutamide solution was mixed with an equal volume of a 5% solution of polyurethane in tetrahydrofuran (THF). Citric acid was then mixed with the silver tolbutamide-polyurethane solution until the molar ratio of silver tolbutamide to citric acid was 1:1.

A catheter was coated with the composition by dipping it for 1 to 3 seconds at ambient temperature and, thereafter, air-drying the catheter to obtain a dried coating of about 0.1 mil in thickness on both the inner and outer surfaces of the catheter. Surfaces of the catheter for which no coating was desired could be shielded during the coating step, via masking or another conventional method.

It will be appreciated that the present invention, as described above, is not limited to the specific compositions shown. Modifications, for example, in the metal ion, sulfonylurea and/or carboxylic acid(s) used, as well as in other components of the composition, and in the method of the present invention are well within the scope of the appended claims.

What is claimed is:

1. A medical device comprising (a) a substrate presenting a surface suitable for contact with a body fluid and (b) an antimicrobial coating provided on said surface, said coating comprising an oligodynamic metal salt of a sulfonylurea, a polymeric material and at least one acid compound selected from the group consisting of a water-soluble carboxylic acid and a water-insoluble carboxylic acid, said device being suitable for extended contact with a body, of a patient or with body fluids.

2. The device of claim 1, wherein said sulfonylurea is tolbutamide, acetohexamide, tolazamide or chlorpropamide.

3. The device of claim 1, wherein said polymeric material has MVTR value in the range of about 100 to 2500 g/m$^2$/ twenty-four hours/mil of membrane thickness.

4. The device of claim wherein said polymeric material comprises polyurethane, polyvinylchloride, nylon, polystyrene, polyethylene, polyvinyl alcohol, polyvinyl acetate, silicone and polyester.

5. The device of claim 1, wherein said water-soluble carboxylic acid is citric acid, glutamic acid, glucoheptonic acid, acetic acid, propionic acid or butyric acid.

6. The device of claim 1, wherein said water-insoluble carboxylic acid comprises stearic acid, capric acid, lauric acid, myristic acid, palmitic acid, arachidic acid, cholic acid, deoxycholic acid, taurocholic acid or glycocholic acid.

7. The device of claim 1, wherein said acid compound is present in an amount rendering said coating light-stable and effecting controlled release of metal ions from said coating.

8. The device of claim 1, wherein said acid compound is present in a molar ratio, relative to said metal salt, that ranges up to about 3:1.

9. The device of claim 1, wherein said metal salt of a sulfonylurea contains at least one metal selected from the group consisting of silver, gold, zinc, platinum and copper.

* * * * *